United States Patent
Van Delden

(10) Patent No.: US 11,591,764 B2
(45) Date of Patent: Feb. 28, 2023

(54) SYSTEM FOR IMPRESSED CURRENT CATHODIC PROTECTION

(71) Applicant: KONINKLIJKE PHILIPS N.V., Eindhoven (NL)

(72) Inventor: Marc Van Delden, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 757 days.

(21) Appl. No.: 16/471,018

(22) PCT Filed: Dec. 20, 2017

(86) PCT No.: PCT/EP2017/083790
§ 371 (c)(1),
(2) Date: Jun. 19, 2019

(87) PCT Pub. No.: WO2018/115108
PCT Pub. Date: Jun. 28, 2018

(65) Prior Publication Data
US 2020/0109478 A1   Apr. 9, 2020

(30) Foreign Application Priority Data

Dec. 20, 2016  (EP) .................................... 16205220
Jul. 18, 2017  (EP) .................................... 17181802

(51) Int. Cl.
*E02B 17/00* (2006.01)
*A61L 2/10* (2006.01)
(Continued)

(52) U.S. Cl.
CPC ............ *E02B 17/0026* (2013.01); *A61L 2/10* (2013.01); *A61L 2/26* (2013.01); *B08B 17/02* (2013.01);
(Continued)

(58) Field of Classification Search
CPC ...... C23F 13/02–13/22; C23F 2213/31; B63B 59/04; E02B 17/0026
See application file for complete search history.

(56) References Cited

U.S. PATENT DOCUMENTS

2006/0065551 A1   3/2006  Howard et al.
2013/0048877 A1*  2/2013  Thoren ................... B08B 17/02
                                                              250/492.1
(Continued)

FOREIGN PATENT DOCUMENTS

KR      130054005 B1 *  1/2014
WO      2017109063 A1   6/2017

OTHER PUBLICATIONS

International Search Report for PCT/EP2017/083790 dated Mar. 12, 2018.
(Continued)

*Primary Examiner* — Alexander W Keeling

(57) ABSTRACT

A system provides impressed current cathodic protection (ICCP) of a marine structure (50) and powers a load in a load arrangement (100) arranged on the marine structure (50) and in contact with the water (10). The power source provides a supply current to generate an electrical potential of the marine structure. The load arrangement (100) has an electrode arranged (130) to extend from the load arrangement into the water for transferring the supply current via the water. The load (20) is coupled between the electrode (130) and a power node (120). The power source is connected to the marine structure and to the power node. The load arrangement is arranged to use the supply current to provide power to the load. Thereto the supply voltage may have an AC component at a high frequency. The load may be an UV-C LED for emitting anti-fouling light.

16 Claims, 4 Drawing Sheets

(51) Int. Cl.
- *A61L 2/26* (2006.01)
- *B08B 17/02* (2006.01)
- *B63B 59/08* (2006.01)
- *C23F 13/02* (2006.01)
- *B63B 59/04* (2006.01)
- *C23F 13/04* (2006.01)
- *C23F 13/16* (2006.01)
- *C23F 13/20* (2006.01)
- *H02J 50/05* (2016.01)
- *B63B 35/44* (2006.01)
- *G01N 17/02* (2006.01)

(52) U.S. Cl.
CPC .............. *B63B 35/44* (2013.01); *B63B 59/04* (2013.01); *B63B 59/08* (2013.01); *C23F 13/02* (2013.01); *C23F 13/04* (2013.01); *C23F 13/16* (2013.01); *C23F 13/20* (2013.01); *G01N 17/02* (2013.01); *H02J 50/05* (2016.02); *A61L 2202/11* (2013.01); *B63B 2035/4433* (2013.01); *C23F 2213/31* (2013.01)

(56) References Cited

U.S. PATENT DOCUMENTS

2013/0228471 A1* 9/2013 Boe .................. C23F 13/20
    205/726
2017/0190397 A1  7/2017 Salters et al.
2018/0201526 A1* 7/2018 Chew ................ C23F 13/04

OTHER PUBLICATIONS

"The 10 most frequently asked questions about corrosion" by David Moran, Corrintec Ltd (paper presented at International seminar for the construction, management and operation of luxury yachts; Project 2002—Amsterdam—Holland 2002).

"Low Signature Impressed Current Cathodic Protection—New Developments—Future Concepts" by Barry Torrance, Aish Technologies Limited, Poole UK (Paper presented at 'Underwater Defence Technology Europe', Amsterdam, Jun. 2005 and at 'Recent Advances in Cathodic Protection', University of Manchester, Feb. 2006).

"Transient nanobubbles in short-time electrolysis" by Vitaly B Svetovoy, Remco G P Sanders and Miko C Elwenspoek; Journal of Physics: Condensed Matter 25 (Apr. 18, 2013).

\* cited by examiner

SYSTEM FOR IMPRESSED CURRENT CATHODIC PROTECTION

CROSS-REFERENCE TO PRIOR APPLICATIONS

This application is the U.S. National Phase application under 35 U.S.C. § 371 of International Application No. PCT/EP2017/083790, filed on Dec. 20, 2017, which claims the benefit of EP Patent Application No. EP 17181802.4, filed on Jul. 18, 2017 and EP 16205220.3 filed Dec. 20, 2016. These applications are hereby incorporated by reference herein.

FIELD OF THE INVENTION

The invention relates to a system for impressed current cathodic protection. The system comprises a power source and a load arrangement to be arranged on a marine structure that is to be in contact with water. The power source is arranged to generate an electrical potential of the marine structure with respect to the water for the impressed current cathodic protection. The load arrangement may receive a supply current from the power source.

BACKGROUND OF THE INVENTION

Structures having metal parts, such as ships, oil rigs, but also jetties, heat exchange units, sea chests in ships, wind turbine at sea, tidal wave electrical generators, etc, operating in natural water such as sea water or fresh water in lakes or rivers, are called marine structures in this document. To counter natural corrosion such marine structures may be coated or painted. Also, such marine structures are often equipped with passive or active cathodic protecting systems. So, bare metal is protected against corrosion, also when protective coat or paint fails locally. Passive cathodic protecting systems use sacrificial Zinc, Aluminum or Iron anodes that dissolve electro-chemically over time, whereas active cathodic protecting systems impress a DC current in using anodes made of MMO-Ti (mix metal oxides) coated Titanium or Pt/Ti (Platinum coated Titanium). The active system that impresses a DC current into the water for generating an electrical potential of the marine structure with respect to the water, is called impressed current cathodic protection or ICCP.

Document US 2006/0065551 describes a corrosion tester for testing the level of protection of metallic structures protected by ICCP. Powering an ICCP system is not described as such, but power may be provided from a ship's battery. Power for operating the corrosion meter may be provided by a built-in battery.

SUMMARY OF THE INVENTION

Various types of electrical loads may need to be placed at the surface of marine structures. For example, such loads may be sensors or active elements that monitor or affect the water, measure various parameters and/or actively control conditions at the surface of the marine structure. For example, the loads may be UV light sources like UV LEDs to counter biofouling. The loads may be embedded in a carrier and need to be powered from an electrical power source.

An assembly of one or more of such loads and electrical circuitry and wiring for powering the loads is called a load arrangement in this document. The assembly may have a carrier or any other type of enclosure as a mechanical element that physically carries one or more loads and said power circuitry. For connecting respective loads to a power source, connections have to be made, e.g. using power lines and power connectors, which is expensive and unreliable.

The invention has as an object to provide an ICCP system that is able to provide power to loads on a surface of a marine structure in a convenient and reliable way.

According to the invention, a system is provided for impressed current cathodic protection (ICCP) of a marine structure in contact with water. The system comprises a power source arranged to provide a supply current to generate an electrical potential of the marine structure with respect to the water for the impressed current cathodic protection, and a load arrangement to be arranged on the marine structure and to be in contact with the water. The load arrangement comprises at least one electrode arranged to extend from the load arrangement into the water for transferring the supply current via the water, at least one power node, and at least one load coupled between the electrode and the power node and arranged to get a load current.

The power source has a first pole for connecting to the marine structure and a second pole for connecting to the power node. The load arrangement is arranged to use the supply current to provide the load current. The load arrangement may comprise a carrier sheet carrying a multitude of said electrodes and loads that are interconnected.

According to the invention, a method is provided for impressed current cathodic protection (ICCP) of a marine structure in contact with water,
a power source being arranged at the marine structure,
a load arrangement being arranged on the marine structure and being in contact with the water, the load arrangement comprising at least one electrode arranged to extend from the load arrangement into the water for transferring a supply current via the water, at least one power node, and at least one load coupled between the electrode and the power node and arranged to get a load current, a first pole of the power source being connected to the marine structure and a second pole being connected to the power node. The method comprises providing a supply current from the power source to generate an electrical potential of the marine structure with respect to the water for the impressed current cathodic protection, and using, in the load arrangement, the supply current to provide the load current.

According to the invention, a method is provided for installing a system as defined above, the method comprising attaching at least one load arrangement to a surface of a marine structure to be exposed to water; connecting the second pole of the power source to the at least one power node; and connecting the first pole of the power source to the marine structure for providing a supply current from the power source to generate an electrical potential of the marine structure with respect to the water for the impressed current cathodic protection and to use, in the load arrangement, the supply current to provide the load current.

The above features have the following effect, when the system is installed on a marine structure that is in contact with water. The ICCP system has a power source and a load arrangement arranged on a surface of the marine structure. The power source provides a supply current to generate an electrical potential of the marine structure with respect to the water for the impressed current cathodic protection. Thereto, the power source has a first pole connected to the marine structure and a second pole for connecting to a power node of the load arrangement via a galvanic connection, e.g. a power line or cable.

The load arrangement has at least one electrode arranged to extend from the load arrangement into the water. The load arrangement has the at least one load coupled between the electrode and the power node. The coupling circuitry is arranged to get a load current from the power source to the load. The electrode is arranged for transferring the supply current via the water to the marine structure.

The supply current from power source is conducted from the first pole to the marine structure, via the water, to the electrode. Subsequently, in the load arrangement, the supply current is conducted via coupling circuitry and the load, from the electrode to the power node. Finally, the supply current is conducted from the power node, via a galvanic connection, to the second pole of the power source. So, a dual-function conductive circuit is formed that couples the load to the power source to provide a load current and also provides the ICCP potential. Sequentially, in the conductive circuit starting at the first pole of the power source, the supply current first flows to the marine structure. Next, from the marine structure immersed in the water, the current flows into the water. At this point the electrical potential for ICCP is generated. Next, from the water, the current flows into the electrode which extends into the water. Then, the load current is derived and flows from the electrode to the load and then to the power node. Finally, the current flows from the power node to the second pole of the power source.

Effectively, the load arrangement is arranged to use the supply current to provide the load current. Correspondingly, the power source is arranged to provide additional power for the load, e.g. an AC component and/or an additional DC voltage on top of the voltage required for ICCP. For example, part of the supply current may be conducted via the load constituting the load current, while another part is conducted to the electrode via other elements of the coupling circuitry.

Advantageously, the current required for ICCP is conducted via said galvanic connection and the load arrangement towards the electrode. So, the electrode constitutes the anode of the ICCP system, while at the same time forming a conductive circuit for the supply current which is also used for powering the load. In the conductive circuit, the water constitutes an electrically conductive medium to the electrode. The proposed ICCP system only needs only a single galvanic connection from the power source to the load arrangement to power electrical loads located on the marine structure, and to also provide the current required for ICCP. Moreover, such a single galvanic connection is easy to install, and no wiring errors can be made during installation.

In an embodiment, the load arrangement has a front surface to be in contact with the water, and the at least one electrode is a multitude of electrodes distributed across the front surface. Advantageously, the ICCP current is provided to the water locally by relatively low currents at the respective electrodes distributed across said surface, so avoiding a concentrated high current at a single anode.

In an embodiment, the at least one load is a multitude of loads coupled to the at least one electrode, which loads are distributed across the load arrangement. Advantageously, distributed loads are provided to perform their respective function across the load arrangement, e.g. across a surface of a ship that is covered by the load arrangement. Moreover, when loads and corresponding electrodes are distributed across the surface, a distributed electrode is formed to yield said ICCP.

In an embodiment, the power source is arranged to provide the supply current having a DC component for generating the electrical potential of the marine structure, and an alternating component for providing at least part of the load current, the alternating component alternating at a high frequency that avoids a net contribution to electrochemistry at the at least one electrode. The DC component may be applied with respect to the marine structure. i.e. to have a DC voltage between the water and metallic conductive parts of that marine structure. Effectively, the DC component provides the impressed current required for the ICCP. The alternating component does not contribute to ICCP, and also does avoid a net contribution to electrochemistry at the at least one electrode by being at a sufficiently high frequency. Thereto, the power source may be arranged to provide the alternating component having a frequency in the range of 20 kHz to 200 kHz, and preferably about 100 kHz. The galvanic coupling of the power node to the power source advantageously enables transfer of any type of AC and DC current that is appropriate for the load. Optionally, the DC component may be provided by adjusting a pulse width of pulses of the alternating component.

Also, or alternatively, the DC component may comprise a DC offset. Advantageously, ICCP is provided in combination with loads operating on the surface to be protected, such as UV light sources for anti-fouling. Moreover, when loads and corresponding electrodes are distributed across the surface, a distributed electrode is formed to yield said ICCP. The connection of the power source to the load arrangement enables the power source to yield impressed current cathodic protection of the marine structure via the DC offset added to the supply voltage.

Optionally, the power source is arranged to, in an interval, disable the DC component and/or the alternating component and measure the electrical potential of the marine structure. Also, optionally, the current required for ICCP may be supplied in an ICCP interval, while the current required for the load may be supplied in a further interval, the intervals being repeated as required so as to have both the loads and the ICCP function substantially independently and intermittently. The measurement of the electrical potential may be performed continuously, e.g. while averaging the measurements, or in one or more specific intervals so as to reduce interference of the DC component and/or the alternating component with the measurement.

In an embodiment, the load arrangement comprises a supply circuit to transfer the supply current between the electrode and the power node and to conduct at least part of the supply current via the load for providing the load current. Effectively, when a load requires a current that is smaller than the ICCP current, the supply circuit may conduct part of the ICCP current directly from the power node to the electrode. Optionally, the supply circuit comprises a Zener diode for transferring part of the supply current between the electrode and the power node.

In an embodiment, the load arrangement comprises as at least one carrier sheet carrying a multitude of said electrodes and loads that are interconnected. Advantageously, a sheet shaped carrier can easily be installed on a surface of a marine structure. Optionally, the load arrangement comprises multiple carrier sheets and each sheet having at least one connector element for connecting the power nodes between neighboring sheets. Advantageously, said galvanic connection is conveniently made via the connector elements.

In an embodiment, the load comprises an UV light source for emitting anti-fouling light for anti-fouling of the load arrangement and/or a surface of the marine structure to be in contact with the water, the water being a fouling liquid containing biofouling organisms. Optionally, the load arrangement may comprise an optical medium. In a practical embodiment, the load arrangement may be an optical medium in the form of a slab or sheet, wherein the front surface is an emission surface for emitting the anti-fouling light, while the front and back surfaces of the optical medium are substantially planar and extend substantially parallel to each other. In such embodiment, the optical medium is very well suitable to be applied as a cover to an exposed surface of the marine structure. The load may be a light source to be adapted to emit ultraviolet light, such as an UV LED. A general advantage of using ultraviolet light for anti-biofouling is that the microorganisms are prevented from adhering and rooting on the surface to be kept clean. The light source may be embedded in the optical medium, or may be arranged outside of the optical medium, at a position adjacent the optical medium.

When the light source is adapted to emit ultraviolet light, it is advantageous for the optical medium to comprise an ultraviolet transparent material such as ultraviolet transparent silicone. In a general sense, the fact that the optical medium comprises material that is configured to allow at least part of the anti-fouling light to distribute through the optical medium may be understood such as to imply that the optical medium comprises material that is substantially transparent to the anti-fouling light.

It is a practical possibility for the load arrangement according to the invention to comprise a single optical medium and a plurality of light sources as loads. The medium may also comprise one or more mirrors to reflect light to the emission surface. In such a case, the optical medium of the load arrangement can be of any suitable shape and size, wherein light sources such as LEDs are distributed throughout the optical medium, and wherein the light emitted by each of the light sources is distributed across the emission surface of the optical medium to an optimized extent. The light sources can be arranged in a series of parallel connections to the respective electrodes and power nodes.

The invention is applicable in various contexts. For example, the load arrangement according to the invention may be applied in the context of a marine vessel. Optionally, a marine structure to be exposed to water has a surface comprising the above load arrangement, wherein the load arrangement is attached to said exposed surface, for example the loads comprising UV light sources for anti-fouling of the exposed surface when immersed in a fouling liquid containing biofouling organisms.

The above-described and other aspects of the invention will be apparent from and elucidated with reference to the following detailed description of embodiments.

BRIEF DESCRIPTION OF THE DRAWINGS

These and other aspects of the invention will be apparent from and elucidated further with reference to the embodiments described by way of example in the following description and with reference to the accompanying drawings, in which.

The figures are purely diagrammatic and not drawn to scale. In the Figures, elements which correspond to elements already described may have the same reference numerals.

DETAILED DESCRIPTION OF THE EMBODIMENTS

Figure 1:
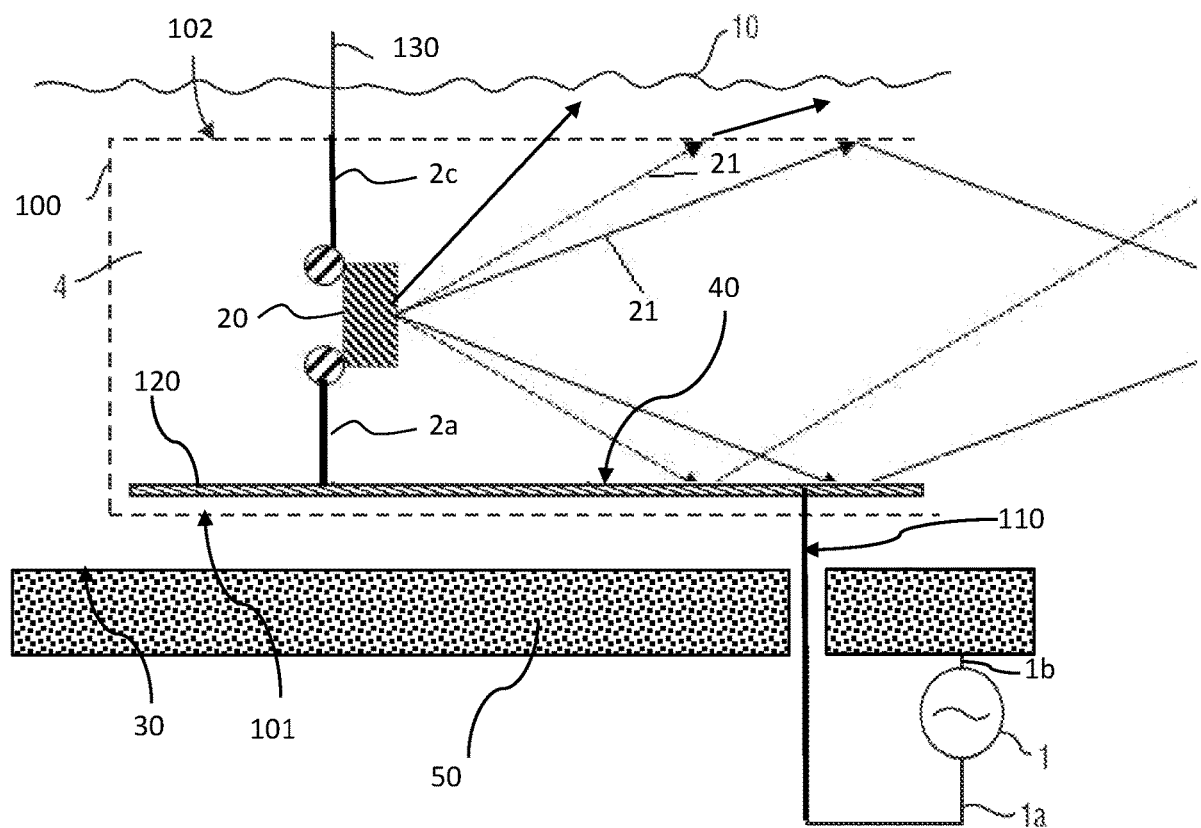
FIG. 1 shows an example of a load arrangement.

The invention relates to a system for corrosion prevention of metallic structures in contact with water, e.g. seawater. When two dissimilar metals (e.g. an iron ship having a bronze propeller) are brought into electrical contact with each other (e.g. by means of propeller shaft bearings or anchors of different iron) and part or all of both metals is brought into contact with (sea)water, one material (the hull) will dissolve more easily than the other (the bronze propeller). Moreover, the more easily dissolvable metal will disappear before the second metal will start to dissolve, usually called rust away. In (sea)water iron dissolves slowly but steadily. Hence, without adequate protection an iron ship will slowly but steadily dissolve and eventually even sink due to hull penetrating holes.

One way to protect an iron ship is to paint it. Yet, as soon as the first paint patch fails, the iron will immediately start to dissolve at that spot. Worse, even a fresh paint coat comes with holes and propeller and rudders in contact with the hull are frequently either unpainted, or stripped from their paint layer due to cavitation in use. Thus, corrosion protection is a must.

To protect a ship from dissolving different protection methods can be applied. A well-known method, passive cathodic protection, requires to bolt an even more dissolvable metal to the marine structure, such as a block of zinc or aluminum. The method operates due to the donation of electrons from the zinc or aluminum to the iron marine structure, with the marine structure thereby acquiring a corrosion inhibiting chemical potential, i.e. as long as the zinc or aluminum is present, protection of the marine structure is ensured and sustained.

A further method to acquire a corrosion inhibiting chemical potential is called impressed current cathodic protection (ICCP) which supplies required electrons by means of a DC power supply. ICCP is aiming at stopping corrosion by creating an electrical potential on the metal to be protected; the potential required being 0.8-0.9 V measured vs. a reference electrode. Electrons are send as a DC current from the impressed current anode towards the marine structure. The material of the anode is selected not to dissolve in (sea)water, e.g. platinum or platinum coated titanium. In the passive system, the flow of electrons is largely self-controlling. In ICCP the flow of current must be controlled, e.g. the current may be temporarily interrupted to measure if the iron has acquired the corrosion inhibiting electrical potential. Control is needed since too many electrons sent to the iron result in water decomposition. Otherwise, hydrogen gas may be formed which in turn can dissolve in the iron, turning it brittle. So-called "over protection" by a too high potential must be avoided. Also, when too little current is applied, corrosion protection is inadequate. As such, controlling the current from the power source based on measuring said electrical potential is well-known in ICCP systems. General background on ICCP systems may further be found in reference documents [1] and [2].

The combination of electricity and water, in particular the rough and tough environment of the off-shore industry, poses a real challenge. Water decomposes under the influence of an electrical current. In the case of sea water, it decomposes under DC current in chlorine and hydrogen gas. Under AC current, both gasses are formed alternatingly at each electrode. Such gasses may enhance the already natural occurring corrosion of the steel ship hull and accelerate the degradation of other materials.

The proposed system achieves ICCP protection in combination with powering a load added in series between the anode and the power supply. Although the power consumption increases due to the load using part of the power, the same level of corrosion protection may be obtained when the same impressed current is generated with or without load. By controlling a DC current based on measuring the electrical potential the marine structure acquires the appropriate electrical potential for ICCP. The load is powered using at least part of the supply current, for example an additional AC current at a high frequency to avoid forming said gasses, as further elucidated below.

In the following, the present invention will be explained with reference to an application scenario, in which the load arrangement is used for powering of UV light sources (in particular LEDs), that may be mounted to the exposed surface of a ship hull to counter bio-fouling. However, any other load on the surface of a marine structure may be powered according to the invention, e.g. a sonar unit or other sensors. Before the details of various embodiments of disclosed subject matter will be explained, the general idea and known approaches to counter bio-fouling in such an application scenario will be discussed.

Biofouling of surfaces which are exposed to water, during at least a part of their lifetime, is a well-known phenomenon, which causes substantial problems in many fields. For example, in the field of shipping, biofouling on the hull of ships is known to cause a severe increase in drag of the ships, and thus increased fuel consumption of the ships. In this respect, it is estimated that an increase of up to 40% in fuel consumption can be attributed to biofouling.

In general, biofouling is the accumulation of microorganisms, plants, algae, small animals and the like on surfaces. According to some estimates, over 1,800 species comprising over 4,000 organisms are responsible for biofouling. Hence, biofouling is caused by a wide variety of organisms, and involves much more than an attachment of barnacles and seaweeds to surfaces. Biofouling is divided into micro fouling which includes biofilm formation and bacterial adhesion, and macro fouling which includes the attachment of larger organisms. Due to the distinct chemistry and biology that determine what prevents them from settling, organisms are also classified as being hard or soft. Hard fouling organisms include calcareous organisms such as barnacles, encrusting bryozoans, mollusks, polychaetes and other tube worms, and zebra mussels. Soft fouling organisms include non-calcareous organisms such as seaweed, hydroids, algae and biofilm "slime". Together, these organisms form a fouling community.

As mentioned in the foregoing, biofouling creates substantial problems. Biofouling can cause machinery to stop working and water inlets to get clogged, to mention only two other negative consequences than the above-mentioned increase of drag of ships. Hence, the topic of anti-biofouling, i.e. the process of removing or preventing biofouling, is well-known.

A light source in the load arrangement may be chosen for anti-fouling to specifically emit ultraviolet light of the C type, which is also known as UVC light, and even more specifically, light with a wavelength roughly between 220 nm and 300 nm. In practice, the peak efficiency is achieved around 265 nm, with a fall-off towards higher and lower wavelengths. At 220 nm and at 300 nm, is has dropped to ~10% efficiency.

It has been found that most fouling organisms are killed, rendered inactive, or rendered unable to reproduce by exposing them to a certain dose of the ultraviolet light. A typical intensity which appears to be suitable for realizing anti-biofouling is 10 mW per square meter. The light may be applied continuously or at a suitable frequency, whatever is appropriate in a given situation, especially at a given light intensity. An LED is one type of UVC lamp which may be applied as the light source of the load arrangement. It is a fact that LEDs can generally be included in relatively small packages and consume less power than other types of light sources. Also, LEDs can very well be embedded in a slab of material. Furthermore, LEDs can be manufactured to emit (ultraviolet) light of various desired wavelengths, and their operating parameters, most notably the output power, can be controlled to a high degree. The LED may be a so-called side-emitting LED, and may be arranged in the optical medium so as to emit the anti-fouling light in directions along the plane of the sheet.

Anti-fouling light may be distributed through an optical medium comprising a silicone material and/or UV grade (fused) silica, and emitting the anti-fouling light from the optical medium and from the surface of a marine structure. UV-C irradiation prevents the (initial) settlement of micro- and macro organisms, for instance on a ship hull. The problem with bio-films is that as their thickness increases over time due to growth of the organisms its surface roughens. Hence, the drag increases, requiring the engine to consume more fuel to maintain the ship's cruising speed, and thus the operational costs increase. Another impact of bio-fouling can be a reduction in the cooling capacity of a pipe radiator or a flow capacity reduction of salt water intake filters and pipes. Therefore, service and maintenance costs increase.

A potential solution to counter bio-fouling of the ship hull can be the coverage of the exterior hull with slabs of for example UV-C transparent materials having embedded UV-C LED(s). These slabs, or generally any load arrangement (i.e. elements or arrangements consuming electrical energy for generating light), are located below the waterline. This is because the submerged surfaces are predominantly sensitive to bio-fouling and, hence, responsible for the increase in drag. Hence, electrical power needs to be delivered under the water-line towards the loads. Obviously, anti-fouling solutions should not render the ICCP system to fail.

Various loads, such as UV LEDs of a biofouling prevention system, require electrical power. UV LEDs are two leaded, polarity sensitive light-sources, which require a DC current to operate. In conventional approaches, wired conductors can be used to provide supply current by means of galvanic contacts. However, traditional fully-wired approaches require complex wiring and connector schemes in order to connect the power source with the loads. A single-wire approach is now described which uses the sea water as a common conductive medium to a power transmitter immersed in the sea water, e.g. (parts of) the metal ship's hull connected to one pole of a power source. Said single wire is provided by a conductor arrangement as described below, which is isolated from said conductive medium.

FIG. 1 shows an example of an ICCP system. The system has a power source 1 and a load arrangement 100. The power source is arranged to provide a supply current to generate an electrical potential of a marine structure 50 with respect to water 10 for the impressed current cathodic protection. The load arrangement 100 is arranged on the marine structure and is in contact with the water 10. The load arrangement has an electrode 130 which extends from the load arrangement into the water, a power node 120, and a load 20. The load is coupled between the electrode 130 and the power node 120 and is arranged to get a load current from the power source.

The power source has a first pole 1b connected to the marine structure and a second pole 1a for connecting to the power node via a conductor arrangement 110, e.g. a power line. In the various embodiments, the supply current from power source is conducted from the first pole to the marine structure, and from the structure's surface, via the water, to the electrode. Subsequently, in the load arrangement, the supply current is conducted from the electrode, via coupling circuitry and the load, to the power node. Finally, the supply current is conducted from the power node, via a galvanic connection, to the second pole of the power source. The galvanic connection may be constituted by any isolated conductor, e.g. a power line, a power strip, a cable or any further conductor arrangement. In the example of FIG. 1, coupling of the load to the electrode and the power node is shown as direct wired connections 2a,2c. The coupling in the load arrangement is arranged to use the supply current to provide the load current. Various other coupling circuits are envisioned and discussed later. The power source is arranged to provide a supply voltage for generating impressed current for ICCP and a load current for powering the load. For example, the supply voltage may have a DC offset to generate the impressed current and an AC component to power the load, as discussed below with reference to FIG. 4. In practice, the power source may have separate units for generating AC and/or DC components, e.g. a rectifier separate from an AC power source to provide a DC component, and possibly further electronic elements for control of the total power and/or measurements.

In the example, the load is a light source 20 for antifouling of a surface 30 of a marine structure 50 exposed to water 10 constituting an electrically conductive medium, for example sea water containing biofouling organisms. The load arrangement 100 may comprise a carrier 4 as indicated by dashed lines. A conductor arrangement 110 is shown to connect the power node 120 to the second pole 1a of the power source. The carrier may have a front surface 102 facing the water and a back surface 101 covering, at least partly, a surface 30 of the marine structure. The load 20 is shown embedded in the carrier and coupled between the power node 120 and the electrode 130 for receiving supply current from the power source 1. The electrode 130 is located at the front surface 101, and is connected to the load via a conductor 2c. The front electrode 130 extends into the water 10 forming an electrically conductive medium. The power node 120 is located at the back surface, and is connected to the load via a conductor 2a.

The conductor arrangement 110 is connected to on pole of the power source 1 via a supply line 1a. For example, the conductor arrangement may have metal strips, a grating or a mesh or another form of isolated conductors distributed across the surface of the marine structure and connected to the power supply. The other pole of the power source is coupled to the marine structure itself having conductive parts immersed in the liquid, e.g. (parts of) the metal ship's hull.

The carrier may comprise an optical medium and be shaped in sheet form. The front surface of the optical medium may constitute an emission surface, and may be substantially planar to the back surface of the carrier, the surfaces extending substantially parallel to each other. The Figure diagrammatically shows a sectional view of a portion of an optical medium, a LED constituting the load embedded in the optical medium, and a mirror 40 that may be present near the back surface of the optical medium. Possible paths of light beams are diagrammatically indicated by means of arrows. The light source may be adapted to emit ultraviolet light, for example an UV-C LED as elucidated in the section above. The optical medium allows at least part of the light to distribute through the optical medium, as shows by the arrows emanating from the light source, propagating and reflecting internally in the layer of the optical medium. In the examples one light source is shown and explained. In practice, the load arrangement may comprise a single optical medium and a plurality of light sources, and a corresponding, associated plurality of mirrors. Each of the mirrors may be electrically coupled to one or more of the light sources.

The mirror may constitute the power node, being electrically conductive and electrically coupled to the load by lead 2a. For example, the mirror is a thin metallic layer of a reflective, conductive metal. At least part of the mirror may be a scattering layer.

In practice, the load arrangement may have multiple loads, e.g. a pattern of multiple light sources and associated electrodes. Multiple mirrors may cover an extended area while substantially provided homogeneous light emission from the emission surface. In such arrangement, electrodes may be shared by multiple loads.

Figure 2:
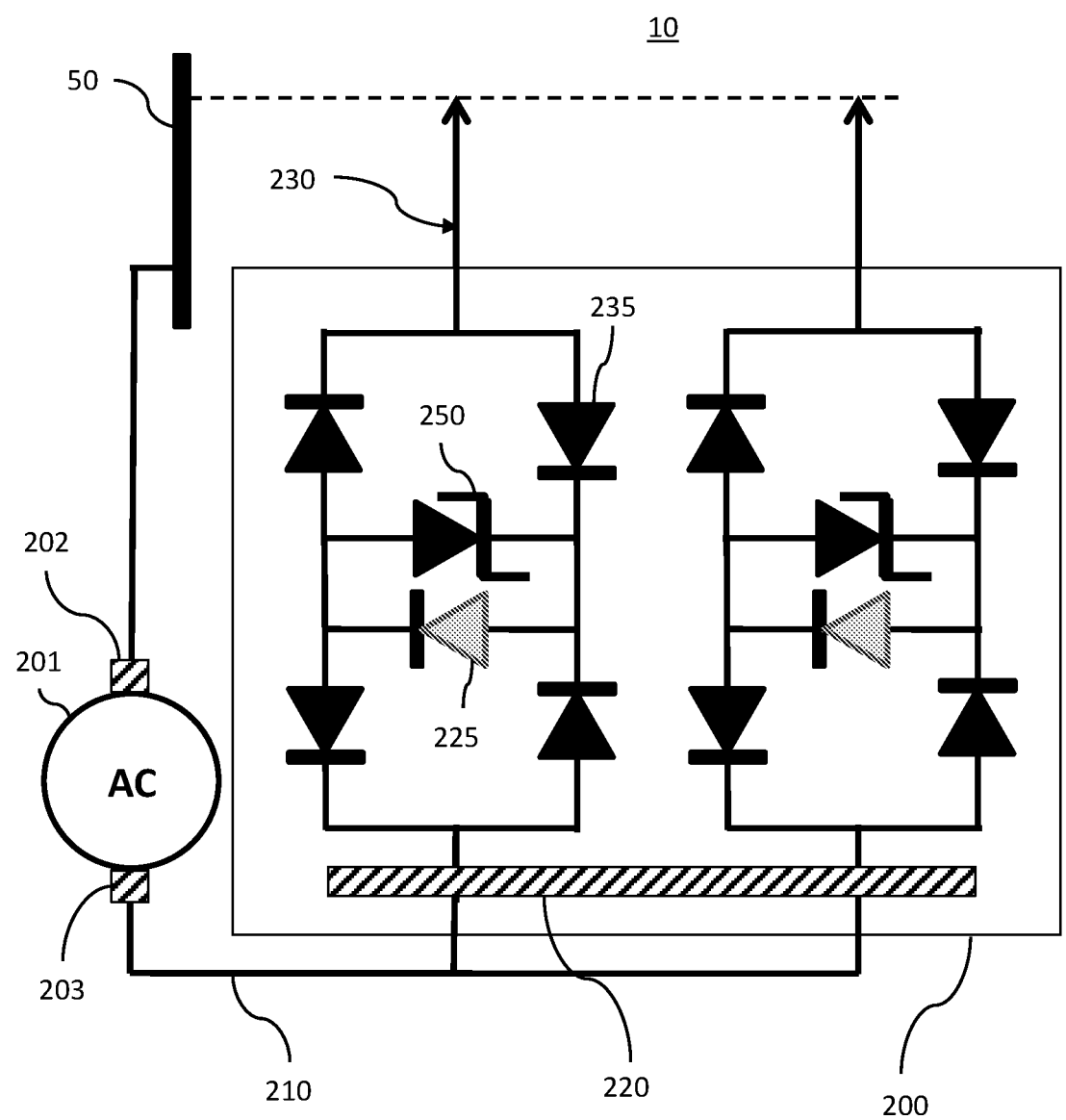
FIG. 2 shows a second example of a load arrangement having a capacitive front electrode.

FIG. 2 shows a second embodiment of an ICCP system that also powers a load. The system has a power source 201 and a load arrangement 200. The power source may include an AC wave form generator, and is arranged to provide a supply current to generate an electrical potential of a marine structure 50 with respect to water 10 for the impressed current cathodic protection. For example, the marine structure may include a ship's exterior hull, a propeller, a rudder, an anchor, etc. The load arrangement 200 is arranged on the marine structure and is in contact with the water 10. The load arrangement has a power node 220, a load 225 and at least one electrode 230, for example made of Pt. The electrodes constitute anodes extending from the load arrangement into the water. A common (sea) water conductive path is formed between the electrodes and the marine structure 50. The load is coupled between the electrode 230 and the power node 220 and is arranged to get a load current from the power source via a rectifier circuit 235, in the example a bridge rectifier of the Graetz type.

The power source has a first pole 202 connected to the marine structure 50 and a second pole 203 for connecting to the power node via a conductor arrangement 210, e.g. a power strip arrangement of isolated metal strips connected to the power node in the load arrangement via connector elements. In practice, the conductor arrangement may need to pass the exterior of the marine structure, e.g. via a ship's hull feedthrough also known as cofferdam.

The supply current from power source is conducted from the first pole to the marine structure, and from the structure's surface, via the water, to the electrode 230. Subsequently, in the load arrangement, the supply current is conducted from the electrode, via the rectifier circuit and the load, to the power node 220. Finally, the supply current is conducted from the power node, via the conductor arrangement, to the second pole 203 of the power source.

The example in FIG. 2 shows two LED strips or sections mounted or adhered at the exterior hull of a ship, which may be painted or may be partly unprotected. Each set of LEDs or strip has at least one seawater contacting anode forming a common seawater return and a common power supply node. The sea water provides a common electrically conductive path to unprotected metal areas of the marine structure 50, e.g. parts of a ship's hull, a propeller or a rudder or other in the sea water submerged metallic regions of the marine structure (e.g. bow thruster tunnel). Effectively, it does not matter how the current flows back from the transmitters towards the hull, scratch, anchor, propeller and other shorts. The elements may be embedded in a carrier, e.g. a silicone enclosure. More seawater anodes and distribution across a larger surface provide a more uniform the corrosion protection and a lower the ship's e-signature.

In FIG. 2, the coupling in the load arrangement is arranged to use the supply current to provide the load current as follows. Any DC or AC component of the supply current is rectified and then conducted to the load, a LED in the example. The DC component provides the current for the ICCP protection, and may be controlled to generate the electrical potential of around 0.8 to 0.9 Volt DC (with respect to a reference electrode) required for ICCP. To measure the hull potential, a reference is needed towards which that potential is measured. This electrode is the so-called reference electrode. The potential of reference electrodes is fixed by chemical composition and various executions of different chemicals and electrode materials exist. As sea water is salt, contains chlorine and is of fairly constant composition, silver/silver-chloride reference electrodes are most suited. For further details see https://www.corrosionpedia.com/an-overview-of-cathodic-protection-potential-measurement/2/2494.1

The AC component is rectified and so provides load current. In the example, the total load current is the sum of the DC component and the rectified AC component. To avoid a net contribution to electro-chemistry, the load arrangement may be operated using AC at a relatively high frequency of 20 kHz to 200 kHz. Limits are determined on the lower-end by the speed of gas formation on water electrolysis, so, in practice at least above 20 kHz, and preferably around 100 kHz.

When it comes to interference, the upper limit may be determined based on the length of a ship or structure to be protected. To prevent radio transmission the wavelength of the generator signal should be less than about 1/10th of the length of the ship. For example, 100 kHz translates to a wavelength of 3000 m in air. The load arrangement may be embedded in silicone having dielectric constant of about 2. So, effectively, the wavelength is suitable for a ship up to 150 m length. With a stern and a bow cofferdam 300 m can be span. If the ship is 75 m long, 200 kHz may be used. As generator costs may increase with power level and frequency, there is a preference to deploy lower frequencies, say 100 kHz. Furthermore, frequencies may be selected that are not reserved for broadcasting or other transmission purposes, i.e. which may be freely used.

In fact, electro-chemistry also occurs at high frequency, but, when the frequency is high enough and the wave form is symmetric, there is no net contribution to the electro-chemistry occurring at the electrodes due to the high-frequency; net contribution meaning a remaining chemical effect. When any asymmetry is introduced, e.g. a net DC offset by a DC bias or asymmetric wave forms, net electro-chemistry does occur at both electrodes. So, electro-chemistry as such does not mean that there is gas formation or deposit. For DC there is a remaining effect; one electrode may show gas formation whereas the other may show the deposit of a solid. In a marine environment of the salt-sea, the deposit may be calcareous. This deposit will not form due to the high frequency AC, but it may form due to the DC component of ICCP. A further description of avoiding a net contribution to electro-chemistry may, for example, be found in document [3], describing frequencies and pulse shapes in relation to electro chemistry.

Effectively, driving the LEDs via the AC component enables independent control of ICCP and LEDs. For example, when the wave form for the LEDs is symmetric there is no net current contribution to the ICCP, and a separate a DC offset current can be provided for ICCP. Alternatively, when the LEDs are driven using asymmetric AC wave forms, a separate DC offset may be omitted.

In an embodiment, the current required for the load may be about equal or smaller than the current required for ICCP. Thereto, the load arrangement may have a supply circuit to transfer any excess supply power between the electrode and the power node. Excess power means a part of the supply current that is not required for the load, while a useful part of the supply current is conducted via the load for providing the load current. So, the supply circuit has the function of over-current protection. For example, the supply circuit may have a controllable bypass circuit, e.g. a controlled FET semiconductor switch, that directly transfers a substantial part of the supply current between the electrode and the power node. In the Figure, the supply circuit is formed by a protective diode 250 that conducts part of the supply current if the voltage across the load exceeds a predetermined maximum. In particular, the supply circuit may comprise a Zener diode for transferring part of the supply current between the electrode and the power node. Also, in case LEDs would fail, ICCP protection can still be sustained by the supply circuit providing a bypass. In practice, such fail safe function may be an important feature.

In a practical embodiment, the above supply circuit may also be applied although the normal operational ICCP current is less than the load current. For example, when a ship's coating is substantially damaged, the ICCP current requirement may strongly increase. The ICCP control unit may now indeed increase the ICCP current, because the supply circuit will function as an overcurrent protection for the load.

For many types of load the current required may be substantially larger than the current for ICCP. Such load current may be provided via said AC component, while the load is able to use AC current directly, or by adding a rectifier. The power source may generate the AC component by a sequence of pulses, e.g. positive and negative pulses. A DC component may be generated by a DC offset and a symmetric AC wave or pulse sequence. Also, a DC component may be achieved by pulse modulation, e.g. height, width, time controlled, a-periodical or any combination thereof.

In an embodiment, the DC component for ICCP is provided by an asymmetry in positive and negative pulses of the supply voltage. The asymmetry is achieved by modulating pulse widths, and/or pulse shapes, of the respective pulses. As a result, the marine structure is charged and discharged, having a net resulting charge due to the asymmetry.

In a further embodiment, the power source is arranged to, in an interval, disable the DC component and/or the alternating component and measure the electrical potential of the marine structure. Measurements of a hull electrical potential may only be done when the hull itself is providing the potential. The ship may be construed as a floating battery that must always be charged to a required potential. If the potential is below the target, the DC component may be increased and vice versa.

In a further embodiment, the current required for ICCP may be supplied in an ICCP interval, while the current required for the load may be supplied in a load interval. The ICCP and load intervals may be repeated as required so as to control both the load function and the ICCP function substantially independently and intermittently. For example, temporarily switching off UV light sources in short intervals will not hamper anti-fouling.

In a further embodiment, measurement intervals may be inserted in such a sequence at regular moments to detect whether the DC component is to be changed. Also, measurements may be executed during specific intervals so as to reduce interference of the DC component and/or the alternating component with the measurement. It is to be noted that the DC component may be constituted by a substantially constant DC current component that is intermittently adjusted based on such measurements, e.g. at said regular moments. In practice, large marine structures behave somewhat like a large battery that is charging and discharging, which is a relatively slow phenomenon. Alternatively, the measurement of the electrical potential may be performed continuously, e.g. while averaging the measurements.

Optionally, the carrier may be shaped as a tile and comprise multiple of said loads. The loads may have interconnected power nodes. In the case of multiple carriers, e.g. a tiling of an anti-fouling layer, the conductor arrangement may have further wires to be connected from tile to tile. For this purpose, below the layer of tiles, a conductor arrangement may have a separate layer of a wire mesh, fishbone or similar pattern that is locally galvanic coupled to the power nodes of the anti-fouling tiles on top of this conductor layer.

Alternatively, a grid of local interconnection patches in a layer below the tiles can be used to connect with complementary parts in the tiles. For example, the load arrangement may have connector elements corresponding to edges of the tile for interconnecting neighboring tiles. The carriers may be provided with connector elements on the edges, while the conductor arrangement has complementary connector elements on positions corresponding to the edges.

Figure 3:
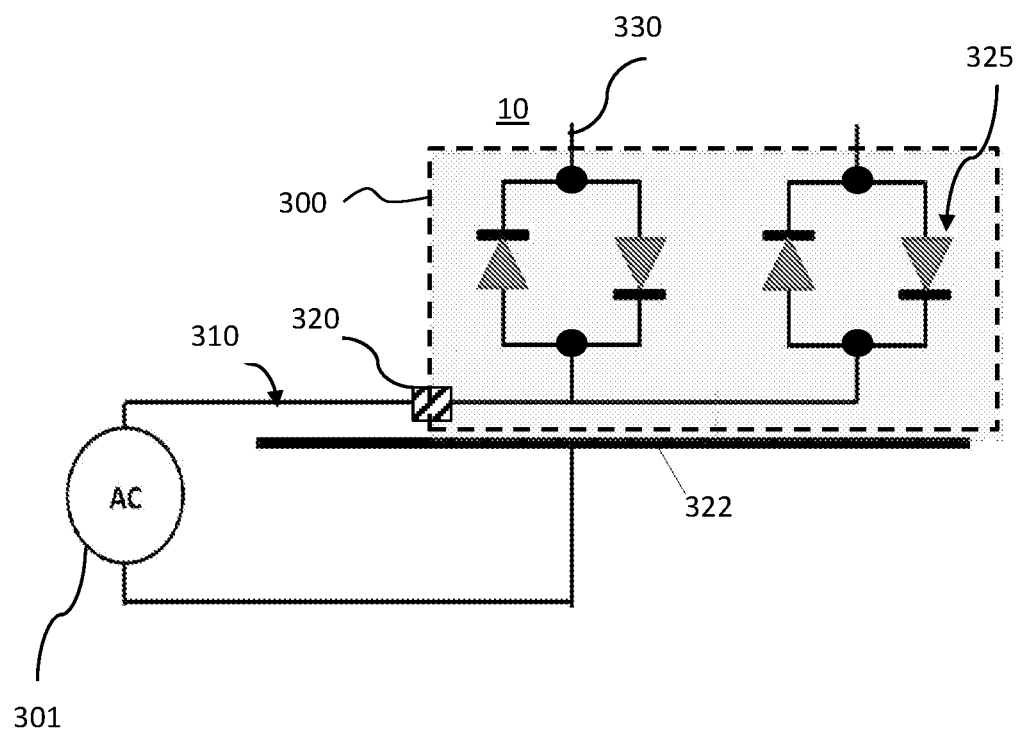
FIG. 3 shows a third example of a load arrangement having a galvanic front electrode.

FIG. 3 shows a third example of a load arrangement having a galvanic front electrode. In the example, the load is a set 325 of anti-parallel UV-C LEDs for emitting anti-fouling light coupled between the electrodes and the power nodes shown as black dots. The load arrangement comprises a carrier 300 as indicated by dashed lines and a conductor arrangement 310 shown as a conductor coupled to a connector 320. In a practical embodiment, the conductor arrangement may have metallic conductors arranged in a pattern distributed across the surface of the marine structure for coupling to a multitude of connector elements of one or more carriers. The connector elements may be located at the back side and/or the edges of the load arrangement. The conductor arrangement may have a multi-lead cable configured to connect the leads to one pole of the power source and for separating and distributing the leads across the surface of the marine structure for coupling to a multitude of connector elements. Alternatively, the conductor arrangement may have a wire-mesh structured for coupling to a multitude of connector elements in a multitude of carriers and distributing the wire-mesh across the surface of the marine structure. The connector elements may be arranged for galvanic coupling to the metallic conductors.

The load arrangement may be similar to the example shown in FIG. 2, and has electrodes 330 constituted by wire electrodes, e.g. made of Pt/Ti, that extend into the liquid 10. In this way, the electrodes constitute a conductive electrical connection via the sea water to a power source 301.

Powering the loads is combined in the ICCP system, which may be installed on the marine structure. The ICCP may be independently powered using DC current from the power source 301 or a separate ICCP power source. To avoid overcurrent situations and electro-chemistry, the load arrangement may be operated using AC at a relatively high frequency, whereas the ICCP related part is operated DC. Thus, independent control over load arrangement and ICCP is possible while still using the same wired infra-structure, which reduces cost. The high frequency chosen for the powering of the LED's avoids that electro-chemistry occurs by AC currents to the LEDs. On the other hand, the ICCP system only requires low currents, which may flow via the LEDs. So, the ICCP currents are not significantly affecting the UVC LED output for anti-fouling. Beneficially, the ICCP structure may be provided with a distributed set of anodes constituted by transmitters (electrodes 330) extending into the seawater, which improves reliability of the corrosion protection. Also, rather than a few discrete anodes conducting highly concentrated ICCP currents, said multiple anodes conducting low ICCP currents are distributed across the hull, thereby reducing electro and magnetic signatures of a vessel.

For electric safety and continued operation when damaged, the common supply wiring in the conductor arrangement may be made redundant, well-isolated and fused. In the case of supply wire damage, one or more not current-limited short-circuits may arise towards the seawater and, hence, to the rudder and/or propeller (shaft) or directly to the hull. Redundant and/or fused supply lines may then be disabled, e.g. disconnected from the supply lines of the conductor arrangement. For example, carriers having multiple loads may also have multiple connections via connector elements to different parts of the conductor arrangement. When some of such parts are disabled, power may still be provided via other parts of the conductor arrangement or via one or more loop-through connections to other carriers. Loop-through may provide a method for maintaining the electrical connection to most of the tiles while some connections inside or towards other tiles are broken. Similar redundancy occurs if parts of a mesh wire in the supporting layer are broken. However, a damage might also lead to a direct electrical connection between a main power lead and the seawater or the hull. For this situation, a current limiting or fusing approach is proposed.

Figure 4:
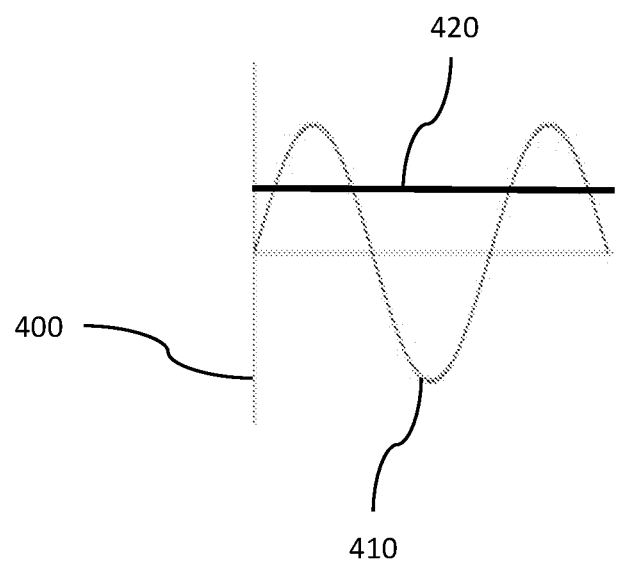
FIG. 4 shows output voltage of a power source.

FIG. 4 shows output voltage of a power source. In a schematic diagram 400 supply voltage is shown in vertical direction along the Y axis, and time is shown horizontally along the X-axis. The output voltage may be generated by the power source 1, 201, 301 as shown in FIG. 1, 2 or 3. FIG. 4 shows an AC component 410 as a symmetric sine wave and a DC component 420 as a constant voltage DC offset to yield ICCP. The frequency of the sine wave may be around 100 kHz It will be clear to a person skilled in the art that the invention is not limited to the examples discussed in the foregoing, but that several amendments and modifications thereof are possible. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species". Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

Finally, use of the above system is foreseen, in particular use of the load arrangement installed to an exposed surface of a marine structure for anti-fouling of the exposed surface when immersed in a fouling liquid containing biofouling organisms. So, the load arrangement according to the invention may be applied on a vessel's hull. Other examples of the exposed surface include the exterior surface of box coolers, surfaces of subsea off-shore equipment, interior walls of water reservoirs like ballast tanks of vessels, and filter surfaces of filter systems in desalination plants.

Summarizing, an ICCP system provides impressed current cathodic protection of a marine structure and powers a load in a load arrangement arranged on the marine structure and in contact with the water. The power source provides a supply current to generate an electrical potential of the marine structure. The load arrangement has an electrode arranged to extend from the load arrangement into the water for transferring the supply current via the water. The load is coupled between the electrode and a power node. The power source is connected to the marine structure and to the power node. The load arrangement is arranged to use the supply current to provide power to the load. Thereto the supply voltage may have an AC component at a high frequency. The load may be an UV-C LED for emitting anti-fouling light.

REFERENCE DOCUMENTS

[1] "The 10 most frequently asked questions about corrosion" by David Moran, Corrintec Ltd (paper presented at International seminar for the construction, management and operation of luxury yachts; Project 2002—Amsterdam—Holland 2002)
[2] "'Low Signature Impressed Current Cathodic Protection—New Developments—Future Concepts" by Barry Torrance, Aish Technologies Limited, Poole UK (Paper presented at 'Underwater Defence Technology Europe', Amsterdam, June 2005 and at 'Recent Advances in Cathodic Protection', University of Manchester, February 2006)
[3] "Transient nanobubbles in short-time electrolysis" by Vitaly B Svetovoy, Remco G P Sanders and Miko C Elwenspoek; Journal of Physics: Condensed Matter 25 (18.04.2013)

The invention claimed is:

1. A system for impressed current cathodic protection of a marine structure, the system comprising
a power source,
wherein the power source is arranged to provide a supply current,
wherein the supply current is arranged to generate an electrical potential of the marine structure with respect to water; and
a load arrangement, the load arrangement comprising:
at least one electrode,
wherein the at least one electrode is arranged to extend from the load arrangement into the water,
wherein the at least one electrode is arranged to transfer the supply current via the water,
at least one power node; and
at least one load,
wherein the at least one load is electrically coupled between the at least one electrode and the at least one power node,
wherein the load is arranged to get a load current, wherein the power source has a first pole and a second pole,
wherein the first pole is connected to the marine structure,
wherein the second pole is connected to the power node,
wherein the load arrangement is arranged to use the supply current to provide the load current,
wherein the load structure is arranged on the marine structure,
wherein the load structure is in contact with the water.

2. The system as claimed in claim 1,
wherein the load arrangement has a front surface,
wherein the front surface is in contact with the water,
wherein the at least one electrode is a plurality of electrodes distributed across the front surface.

3. The system as claimed in claim 1,
wherein the at least one load is a plurality of loads,
wherein the plurality of loads is coupled to the at least one electrode,
wherein the plurality of loads is distributed across the load arrangement.

4. The system as claimed in claim 1, wherein the power source is arranged to provide the supply current, the supply current comprising:
a DC component, wherein the DC component generates the electrical potential of the marine structure with respect to the water; and
an alternating component, wherein the alternating component is arranged to provide at least part of the load current,
wherein the alternating component alternates at a high frequency such that the alternating component avoids a net contribution to electro-chemistry at the at least one electrode.

5. The system as claimed in claim 4,
wherein the alternating component generates pulses,
wherein the DC component generates a DC offset,
wherein the DC offset is provided by adjusting a pulse width of the pulses.

6. The system as claimed in claim 1,
wherein the power source is arranged to provide an alternating component,
wherein the alternating component has a frequency in the range of 20 kHz to 200 kHz.

7. The system as claimed in claim 4, wherein the power source is arranged to disable the DC component.

8. The system as claimed in claim 1,
wherein the load arrangement comprises a supply circuit,
wherein the supply circuit is arranged to transfer the supply current between the at least one electrode and the at least one power node,
wherein the supply circuit is arranged to conduct at least part of the supply current via the load to provide the load current.

9. The system as claimed in claim 8,
wherein the supply circuit comprises a Zener diode, wherein the Zener diode is arranged to transfer a portion of the supply current between the at least one electrode and the at least one power node.

10. The system according to claim 1,
wherein the load comprises an UV light source,
wherein the UV light source is arranged to emit anti-fouling light for anti-fouling of the load arrangement.

11. A marine structure the marine structure comprising:
the system as claimed in claim 1,
wherein the marine structure has a first surface,
wherein the load arrangement is arranged on the first surface,
wherein the first pole of the power source is connected to the marine structure,
wherein the first pole of the power source is arranged to transfer the supply current from the power source to the load arrangement,
wherein the first surface is exposed to the water,
the second pole of the power source is galvanically connected to the at least one power node.

12. The system as claimed in claim 4,
wherein the alternating component generates pulses,
wherein the DC component generates a DC offset,
wherein the DC component is provided by adjusting a pulse width of the pulses.

13. The system as claimed in claim 4, wherein the power source is arranged to disable the alternating component.

14. A method of enabling a measurement of the electrical potential of a marine structure, the marine structure comprising:
a power source,
wherein the power source is arranged to provide a supply current,
wherein the supply current is arranged to generate an electrical potential of the marine structure with respect to water; and
a load arrangement, the load arrangement comprising:
at least one electrode,
wherein the at least one electrode is arranged to extend from the load arrangement into the water,
wherein the at least one electrode is arranged to transfer the supply current via the water,
at least one power node; and
at least one load,
wherein the at least one load is electrically coupled between the at least one electrode and the at least one power node,
wherein the load is arranged to get a load current,
wherein the power source has a first pole and a second pole,
wherein the first pole is connected to the marine structure,
wherein the second pole is connected to the power node,
wherein the load arrangement is arranged to use the supply current to provide the load current,
wherein the load structure is arranged on the marine structure, wherein the load structure is in contact with the water,
wherein the marine structure has a first surface,
wherein the load arrangement is arranged on the first surface,
wherein the first pole of the power source is connected to the marine structure,
wherein the first pole of the power source is arranged to transfer the supply current from the power source to the load arrangement,
wherein the first surface is exposed to the water,
the second pole of the power source is galvanically connected to the at least one power node,
wherein the power source is arranged to provide the supply current, the supply current comprising:
a DC component, wherein the DC component generates the electrical potential of the marine structure with respect to the water; and
an alternating component, wherein the alternating component is arranged to provide at least part of the load current,
the method comprising:
disabling the DC component; and
measuring of the electrical potential of the marine structure.

15. A method of enabling a measurement of the electrical potential of a marine structure, the marine structure comprising:
a power source,
wherein the power source is arranged to provide a supply current,
wherein the supply current is arranged to generate an electrical potential of the marine structure with respect to water; and
a load arrangement, the load arrangement comprising:
at least one electrode,
wherein the at least one electrode is arranged to extend from the load arrangement into the water,
wherein the at least one electrode is arranged to transfer the supply current via the water,
at least one power node; and
at least one load,
wherein the at least one load is electrically coupled between the at least one electrode and the at least one power node,
wherein the load is arranged to get a load current,
wherein the power source has a first pole and a second pole,
wherein the first pole is connected to the marine structure,
wherein the second pole is connected to the power node,
wherein the load arrangement is arranged to use the supply current to provide the load current,
wherein the load structure is arranged on the marine structure, wherein the load structure is in contact with the water,
wherein the marine structure has a first surface,
wherein the load arrangement is arranged on the first surface,
wherein the first pole of the power source is connected to the marine structure,
wherein the first pole of the power source is arranged to transfer the supply current from the power source to the load arrangement,
wherein the first surface is exposed to the water,
the second pole of the power source is galvanically connected to the at least one power node,
wherein the power source is arranged to provide the supply current, the supply current comprising:
a DC component, wherein the DC component generates the electrical potential of the marine structure with respect to the water; and
an alternating component, wherein the alternating component is arranged to provide at least part of the load current, the method comprising:
disabling the alternating component; and measuring of the electrical potential of the marine structure.

16. The system according to claim 10,
wherein a surface of the marine structure is in contact with the water,
wherein the water is a fouling liquid containing biofouling organisms.

\* \* \* \* \*